United States Patent [19]

Suami

[11] 4,148,921

[45] Apr. 10, 1979

[54] ANTITUMOR AGENTS

[76] Inventor: Tetsuo Suami, 3-5-8 Nakamachi, Musashimo, Tokyo 180, Japan

[21] Appl. No.: 815,119

[22] Filed: Jul. 13, 1977

[51] Int. Cl.$^2$ .................. A61K 31/17; A61K 31/175; C07C 127/15; C07C 133/06

[52] U.S. Cl. ................. 424/322; 260/553 R; 260/554; 424/323

[58] Field of Search .................. 260/553 R, 554; 424/322, 323

[56] References Cited

U.S. PATENT DOCUMENTS 4,039,578  8/1977  Suami .................. 260/553 R

FOREIGN PATENT DOCUMENTS 754895  5/1976  South Africa .................. 260/553 R

OTHER PUBLICATIONS

Suami et al., "Bull. of the Chem. Soc. of Jap.", vol. 43, pp. 2953-2956 (1970).
Machinami et al. (I), "Bull. of the Chem. Soc. of Jap.", vol. 48(12), pp. 3763-3764 (1975).
Johnston et al., "J. Med. Chem.", vol. 18(1), pp. 104-106 (1975).
Machinami et al. (II), "Bull. of the Chem. Soc. of Jap.", vol 48(12) pp. 3761-3762 (1975).

*Primary Examiner*—Winston A. Douglas
*Assistant Examiner*—John Doll

*Attorney, Agent, or Firm*—David M. Morse

[57] ABSTRACT

Novel inosadiamine derivatives of the formula

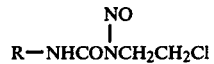

wherein R represents

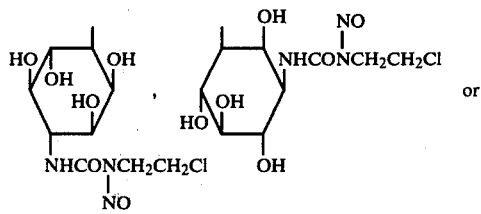

or

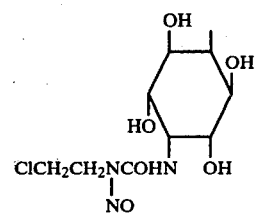

exhibit high effectiveness against various mammalian tumor systems.

6 Claims, No Drawings

ANTITUMOR AGENTS

BACKGROUND OF THE INVENTION (1) Field of the Invention

This invention relates to novel inosadiamine derivatives useful as antitumor agents.

(2) Description of the Prior Art

Cancer is now the second leading cause of death in the United States and it is believed that the proportion of deaths due to cancer will climb in coming years throughout the world due to such factors as the increase in the average life span, the large number of persons completing 20–30 years as active smokers, environmental carcinogens and the more widespread use of various preservatives in foods and other substances which are ingested. The trend in cancer therapy is now in the direction of earlier and more universal use of chemotherapy alone or in conjunction with radiation and surgery, in contrast to previous use of chemotherapy as a last resort in surgically inoperative cases.

Various nitrosourea compounds have been disclosed in the literature as active therapeutic agents for the treatment of experimental and clinical neoplasms. The three members of this class which have been clinically studied are BCNU [1,3-bis(2-chloroethyl)-1-nitrosourea], CCNU [1-(2-chloroethy)-3-cyclohexyl-1-nitrosourea] and methyl CCNU [1-(2-chloroethyl)-2-(4-methylcyclohexyl)-1-nitrosourea]. These compounds have been shown to have activity either alone or in combination with other agents against primary brain tumors, malignant melanoma, lymphomas and a few selected solid tumors.

Montgomery et al. have disclosed in *J. Med. Chem.*, 18(1), 104 (1975) the preparation of a streptozotocin analog of the formula

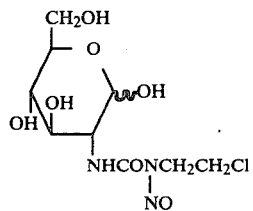

in which a 2-chloroethyl group was substituted for the methyl group of the N-nitrosourea moiety in streptozotocin. The new analog named chlorozotocin is reported to possess enhanced effectiveness against leukemia L1210 relative to streptozotocin.

The inosadiamine derivative of the formula

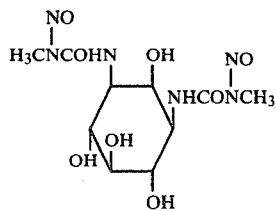

was disclosed by Suami et al. in *Bull. Chem. Soc. Japan*, 43(9), 2953 (1970) as being active against Ehrlich ascites tumor and Hela carcinoma.

Suami et al. have also reported preparation of the compound of the formula

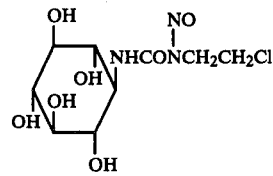

in *Bull. Chem. Soc. Japan*, 48 (12), 3763 (1975). The above compound is said to have activity against L1210 leukemia in mice. Other inosamine nitrosoureas are disclosed in Belgian Pat. No. 832,227 and Japanese Patent Publication J51-52160 (Derwent No. 47028X/25).

SUMMARY OF THE INVENTION

The present invention provides novel antitumor agents having the formula

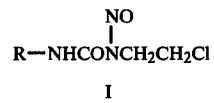

wherein R represents

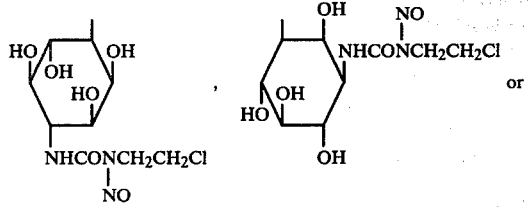

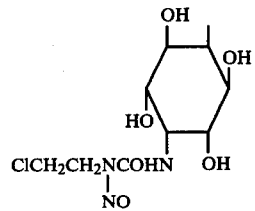

The compounds of formula I inhibit the growth of mammalian tumor systems such as L1210 lymphatic leukemia.

The compounds of the present invention may be prepared by the process comprising the consecutive steps of (1) condensing an inosadiamine selected from myoinosadiamine-1,4, myo-inosadiamine-1,3 or neo-inosadiamine-1,4 with 2-chloroethyl isocyanate in an inert solvent system at a temperature of from about −20° C. to 100° C. to form a carbamoyl intermediate of the formula

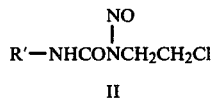

wherein R' represents

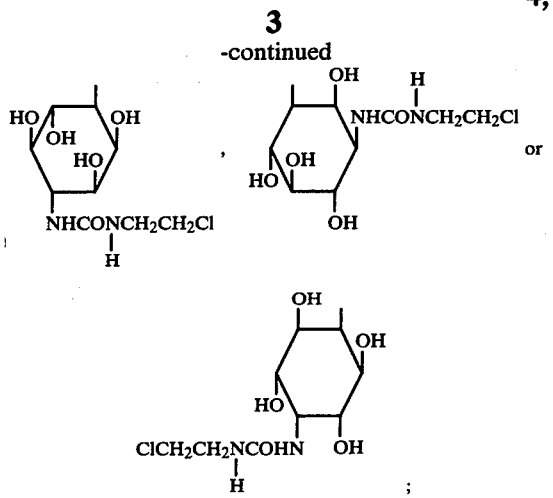

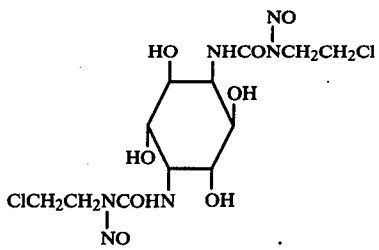

(2) subjecting intermediate II to nitrosation in an inert solvent system at a temperature of from about −20° C. to 50° C. to form the desired compound of formula I.

The inosadiamine-1,4 and inosadiamine-1,3 starting materials are disclosed in the literature. Thus, preparation of myo-inosadiamine-1,4 as its hexaacetyl derivative is reported in *Bull. Chem. Soc. Japan*, 48 (10), 2895 (1975). The free base may easily be obtained from the hexaacetyl derivative by deacetylation as with hydrochloric acid followed by treatment with a basic ion exchange resin such as Amberlite IRA-400 (OH−). Myo-inosadiamine-1,3 in the form of its dihydrochloride is reported in *J. Org. Chem.*, 33, 2831 (1968). The dihydrochloride may be converted to the free base starting material by treatment with a basic ion exchange resin, e.g. Amberlite IRA-400 (OH−). Preparation of neo-inosadiamine-1,4 is reported in *J. Amer. Chem. Soc.*, 83, 2005 (1961).

The condensation step (1) in the above reaction is carried out in an inert solvent system. Examples of suitable inert solvents are water, (lower)alkanols such as methanol, ethanol, propanol or butanol, water-(lower-)alkanol mixtures such as aqueous methanol, aqueous ethanol, etc. and inert organic solvents such as dioxane. The preferred solvent is water. The condensation reaction may be conducted over a wide range of temperatures, i.e. from about −20° C. to 100° C., but is preferably performed at a temperature of around 0° C. and with stirring.

Nitrosation step (2) is carried out according to conventional procedures. Thus, the carbamoyl intermediate II may be reacted in an inert aqueous or organic solvent system (such as described above for the condensation step) with nitrous acid or a source thereof, e.g. by in situ generation from a nitrite such as sodium nitrite, potassium nitrite or amyl nitrite or dinitrogen trioxide and an aqueous organic or mineral acid such as formic acid, acetic acid, propionic acid or hydrochloric acid.

The temperature for the nitrosation reaction may range from about −20° C. to 50° C. and is most preferably about 0° C.

A preferred embodiment of the present invention is the compound having the chemical name di-N,N-(N-2-chloroethyl-N-nitrosocarbamoyl)-neo-inosadiamine-1,4 and the structure

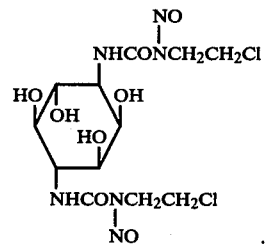

Another preferred embodiment of the present invention is the compound having the chemical name di-N,N-(N-2-chloroethyl-N-nitrosocarbamoyl)-myo-inosadiamine-1,4 and the structure Still another preferred embodiment of the present invention is the compound having the chemical name di-N,N-(N-2-chloroethyl-N-nitrosocarbamoyl)-myo-inosadiamine-1,3 and the structure

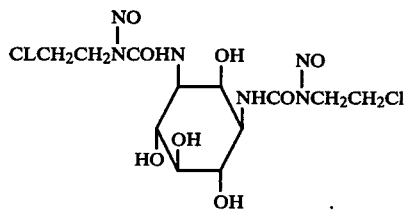

The compounds of the present invention were tested against the transplantable mouse tumor lymphatic leukemia L1210 and the results of these tests are shown below in Tables 1–3. The methodology used generally followed the protocols of the National Cancer Institute [see, for example, *Cancer Chemotherapy Rep.*, 50, 79 (1966) and *Cancer Chemotherapy Rep. Part 3.*, 3, 1–103 (1972)]. The essential experimental details are given at the bottom of each of the tables.

Table 1

| | Effect of Compound TE-8 on L1210 Lymphatic Leukemia | | | | | |
|---|---|---|---|---|---|---|
| | | | Effect | Average | | |
| | Dose | MST | MST | Weight | Survivors | |
| Compound | mg./kg. | Days | % T/C | Change in g. | Day 5 | Day 34 |
| TE-8 | 64 | 6.5 | 93 | −2.9 | 6/6 | 0/6 |
| | 32 | >34.0 | >486 | −1.2 | 6/6 | 5/6 |
| | 16 | 16.0 | 229 | −0.2 | 6/6 | 2/6 |
| | 8 | 15.5 | 214 | +0.6 | 6/6 | 0/6 |
| | 4 | 12.0 | 171 | +0.4 | 6/6 | 0/6 |
| | 2 | 8.0 | 114 | +0.9 | 6/6 | 0/6 |
| | 1 | 7.0 | 100 | +2.8 | 6/6 | 0/6 |

Table 1-continued

Effect of Compound TE-8 on L1210 Lymphatic Leukemia

| Compound | Dose mg./kg. | MST Days | Effect MST % T/C | Average Weight Change in g. | Survivors Day 5 | Survivors Day 34 |
|---|---|---|---|---|---|---|
| | 0.5 | 7.0 | 100 | +2.8 | 6/6 | 0/6 |
| BCNU | 64 | 16.0 | 229 | −3.7 | 6/6 | 2/6 |
| | 32 | >34.0 | >446 | −1.7 | 5/6 | 3/6 |
| | 16 | 12.5 | 179 | +0.8 | 6/6 | 0/6 |
| | 8 | 10.0 | 143 | +0.5 | 6/6 | 0/6 |
| | 4 | 8.5 | 121 | +0.3 | 6/6 | 0/6 |
| | 2 | 8.0 | 114 | +0.9 | 6/6 | 0/6 |
| | 1 | 7.0 | 100 | +2.5 | 6/6 | 0/6 |
| | 0.5 | 7.0 | 100 | +3.2 | 6/6 | 0/6 |
| Control | Saline | 7.0 | — | +2.6 | 10/10 | 0/10 |

Tumor inoculum: $10^6$ L1210 ascitic cells implanted ip
Host: $BDF_1$ ♂ mice
Treatment: Single injection on day 1 given ip
MST = Median survival time in days
Effect: % T/C = MST treated/MST control × 100
Criteria: % T/C = 125 considered significant tumor inhibition (prolongaton of host survival)
Survivors:
 Day 5: Toxicity evaluation; weight change recorded
 Day 34: Experiment terminated, survivors considered "cured", others died of tumor
TE-8 = Compound of Example 1
BCNU = 1,3-bis(2-chloroethyl)-1-nitrosourea

Table 2

Effect of Compounds TE-8 and TE-9 on L1210 Leukemia

| Compound | Dose mg./kg. | MST Days | Effect MST % T/C | Average Weight Change in g. | Survivors Day 5 | Survivors Day 30 |
|---|---|---|---|---|---|---|
| TE-8 | 32 | >21.5 | >307 | −0.5 | 6/6 | 5/6 |
| | 16 | 20.0 | 286 | +0.3 | 6/6 | 2/6 |
| | 8 | 16.0 | 229 | −1.4 | 6/6 | 1/6 |
| | 4 | 11.5 | 164 | +1.1 | 6/6 | 1/6 |
| | 2 | 7.0 | 100 | +1.4 | 4/6 | 0/6 |
| | 1 | 7.5 | 107 | +1.9 | 6/6 | 0/6 |
| TE-9 | 128 | 6.0 | 86 | −4.6 | 6/6 | 0/6 |
| | 64 | 17.5 | 250 | −2.6 | 6/6 | 1/6 |
| | 32 | 15.0 | 214 | +0.3 | 6/6 | 0/6 |
| | 16 | 12.5 | 179 | −0.2 | 6/6 | 0/6 |
| | 8 | 12.0 | 171 | +1.5 | 6/6 | 0/6 |
| | 4 | 8.0 | 114 | +1.7 | 6/6 | 0/6 |
| | 2 | 8.5 | 121 | +1.1 | 6/6 | 0/6 |
| | 1 | 7.0 | 100 | +0.3 | 6/6 | 0/6 |
| BCNU | 32 | 20.0 | 286 | −0.9 | 6/6 | 2/6 |
| | 16 | 15.0 | 214 | −0.1 | 6/6 | 0/6 |
| | 8 | 13.5 | 193 | −0.2 | 6/6 | 0/6 |
| | 4 | 8.5 | 121 | −0.3 | 6/6 | 0/6 |
| | 2 | 7.0 | 100 | 0 | 6/6 | 0/6 |
| | 1 | 7.0 | 100 | +0.2 | 6/6 | 0/6 |
| Control | Saline | 7.0 | — | | 10/10 | 0/10 |

Tumor inoculum: $10^6$ L1210 ascites cells implanted ip
Host: ♂ mice, $BDF_1$
Treatment: Single injection on day 1 given ip
Evaluation: MST = Median survival time in days
Effect: % T/C = MST treated/MST control × 100
Criteria % T/C > 125 considered significant tumor inhibition (prolongation of host survival)
Survivors:
 Day 5 Toxicity evaluation; weight change recorded
 Day 30 Experiment terminated, survivors considered "cured", others died of tumor.
TE-8 = Compound of Example 1
TE-9 = Compound of Example 2

Table 3

Effect of Compounds TE-8 and TE-17 on L1210 Leukemia

| Compound | Dose mg./kg. day | MST Days | Effect MST % T/C | Average Weight Change in g. | Survivors Day 5 | Survivors Day 33 |
|---|---|---|---|---|---|---|
| TE-8 | 32 | 9.5 | 136 | −1.1 | 6/6 | 0/6 |
| | 16 | >33.0 | >471 | −1.2 | 6/6 | 5/6 |
| | 8 | 15.0 | 214 | −0.8 | 6/6 | 0/6 |
| | 4 | 12.0 | 171 | −0.8 | 6/6 | 0/6 |
| | 2 | 10.5 | 150 | −1.1 | 6/6 | 0/6 |
| TE-17 | 128 | 20.5 | 293 | −1.3 | 6/6 | 0/6 |
| | 64 | 20.5 | 286 | −1.6 | 6/6 | 2/6 |
| | 32 | >33.0 | >471 | −1.2 | 6/6 | 3/6 |
| | 16 | 17.0 | 243 | −0.7 | 6/6 | 0/6 |
| | 8 | 12.0 | 171 | −0.8 | 6/6 | 0/6 |
| | 4 | 9.5 | 136 | −1.3 | 6/6 | 0/6 |

Table 3-continued

| | Effect of Compounds TE-8 and TE-17 on L1210 Leukemia | | | | | |
|---|---|---|---|---|---|---|
| | Dose | | Effect | Average | Survivors | |
| Compound | mg./kg. day | MST Days | MST % T/C | Weight Change in g. | Day 5 | Day 33 |
| | 2 | 9.0 | 129 | −0.3 | 6/6 | 0/6 |
| | 1 | 8.0 | 114 | +0.9 | 6/6 | 0/6 |
| BCNU | 32 | >33.0 | >471 | −1.2 | 6/6 | 5/6 |
| | 16 | 19.0 | 271 | −0.9 | 6/6 | 2/6 |
| | 8 | 13.5 | 193 | −0.1 | 6/6 | 1/6 |
| | 4 | 10.0 | 143 | +0.1 | 6/6 | 0/6 |
| | 2 | 8.0 | 114 | +1.2 | 6/6 | 0/6 |
| Control | Saline | 7.0 | — | +2.0 | 10/10 | 0/10 |

Tumor inoculum: $10^6$ L1210 ascites cells implanted ip
Host: ♀ mice, $BDF_1$
Treatment: Single injection on day 1 given ip
Evaluation: MST = *Median survival time in days*
Effect: % T/C = *MST treated/MST control* × 100
Criteria: % T/C > 125 considered significant tumor inhibition (prolongation of host survival)
Survivors:
 Day 5 Toxicity evaluation, weight change recorded
 Day 33 Experiment terminated, survivors considered "cured", others died of tumor.
TE-8 = Compound of Example 1
TE-17 = Compound of Example 3

SUMMARY OF RESULTS

Table 1: In a direct comparative test with BCNU against L1210 leukemia, TE-8 had activity in terms of optimal dose (32 mg./kg./day), minimum effective dose (4 mg./kg./day) and day 34 survivors at least as good as BCNU in all parameters. The toxicity was comparable.

Table 2: Compounds TE-8 and TE-9 were tested in comparison with BCNU. TE-9 appeared to be less toxic than TE-8 (higher optimum dose) and less active as measured by T/C effect and 30 day survivors.

Table 3: Compound TE-17 was tested in comparison with TE-8 and BCNU and appeared to have activity and toxicity very close to that of the latter two compounds. There was some suggestion of a broader therapeutic ratio (TR) (long term survivors observed at 64 mg./kg./day, minimum effective dose 2 mg./kg./day, approximate TR=32).

The compounds of the present invention exhibit effectiveness against malignant mammalian tumor systems as evidenced by the above-mentioned L1210 leukemia tests in mice. They may be administered alone or in combination with other antitumor agents. They are generally administered parenterally in the form of pharmaceutical compositions, i.e. mixtures of a tumor-inhibiting amount of compound I with suitable inert pharmaceutical carriers or diluents.

It will be appreciated that the actual preferred amounts of compound I used will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, route of administration, rate of excretion, condition of the patient, drug combinations, reaction sensitivities and severity of the disease. Optimal dosages for a given set of conditions can be ascertained by those skilled in the art using conventional dosage determination tests in view of the animal data provided and the above guidelines.

The following examples are not limiting but are illustrative of this invention. Amberlite ® IR-120 is a strongly acidic cation exchanger having a styrenedivinylbenzene matrix and marketed by Rohm and Haas, Washington Square, Philadelphia, Pa. Amberlite ® IRA-400 is a strongly basic anion exchanger having a styrenedivinylbenzene matrix which is also marketed by Rohm and Haas Corp.

EXAMPLE 1

Di-N,N-(N-2-chloroethyl-N-nitrosocarbamoyl)-myo-inosadiamine-1,4

(TE-8)

Hexaacetyl myo-inosadiamine-1,4 (1.75 g.)[1] was heated in 6 hydrochloric acid under reflux for 3 hours. After cooling at ambient temperature, the reaction solution was filtered. The filtrate was evaporated under reduced pressure. The residue was dissolved in cold water and the solution was treated with Amberlite IRA-400 (OH−) resin to remove chloride ions. The solution was again evaporated in vacuo to give myo-inosadiamine-1,4 in a quantitative yield.

[1] T. Suami, K. Tadano and S. Horiuchi, *Bull. Chem. Soc. Japan*, 48, 2895-2897 (1975).

The crude base (0.84 g.) was dissolved in water (150 ml.). To the solution, 2-chloroethyl isocyanate (1.7 ml.) was added drop by drop under ice cooling with agitation. The reaction mixture was settled overnight in a refrigerator and a product was collected by filtration. The crude product was washed with ethanol to give 0.74 g. of di-N,N-(N-2-chloroethyl-carbamoyl)-myo-inosadiamine-1,4. The mother liquour was evaporated under reduced pressure to give 0.19 g. of the product as a second crop. M.p. 202°–215° C. (decomp). Total yield was 51% from the free base.

The carbamoyl derivative (1.62 g.) was treated with sodium nitrite (1.73 g.) in 80% formic acid (54 ml.) under ice cooling with agitation. After 2 hours, pale yellow fine crystals were collected by filtration. The crystals were washed with ether and dried in a desicator to give 1.04 g. (56%) of the title compound; m.p. 170° C. (decomp).

Anal Calcd. for $C_{12}H_{20}N_6Cl_2O_8$: C, 32.23; H, 4.51; N, 18.79; Cl, 15.85. Found: C, 32.02; H, 4.38; N, 18.74; Cl, 15.68.

EXAMPLE 2

Di-N,N-(N-2-chloroethyl-N-nitrosocarbamoyl)-myo-inosadiamine-1,3 (TE-9)

myo-Inosadiamine-1,3 dihydrochloride[2] was treated with Amberlite IRA-400 (OH−) resin in water to give myo-inosadiamine-1,3 as crude crystals in a quantitative yield.

[2] T. Suami, S. Ogawa, S. Naito and H. Sano, *J. Org. Chem.*, 33, 2831-2834 (1968).

The free base (138 mg.) was dissolved in cold water (5 ml.), and to the solution, 2-chloroethyl isocyanate (0.26 ml.) was added under ice cooling with agitation. After two hours, crystalline precipitates were collected by filtration to give 326 mg. of a first crop of a product. Evaporation of the filtrate gave another crop of the product (101 mg.). The combined products were recrystallized from a mixture of formic acid (1 ml.) and ethanol (1 ml.) to give 218 mg. (75%) of di-N,N-(N-2-chloroethyl-carbamoyl)-myo-inosadiamine-1,3; m.p. 230°-235° C. (decomp).

Anal Calcd. for $C_{12}H_{22}N_4Cl_2O_6$: C, 37.03; H, 5.70; N, 14.39; Cl, 18.21. Found: C, 37.00; H, 5.54; N, 14.05; Cl, 17.92.

A 287 mg. portion of the carbamoyl derivative was dissolved in 80% formic acid, and to the solution, sodium nitrite (305 mg.) was added under ice cooling with agitation. After 1.5 hours, Amberlite IR-120 (H+) resin was added to the mixture and the mixture was agitated for 30 minutes. The mixture was filtered and the filtrate was evaporated under reduced pressure to give yellow crystalline residue. The residue was washed with ether to give 343 mg. of pale yellow crystals of di-N,N-(N-2-chloroethyl-N-nitrosocarbamoyl)-myo-inosadiamine-1,3 as a crude product; m.p. 115° C. (decomp).

A part of the title product was acetylated with acetic anhydride in pyridine to give the tetra-O-acetyl derivative as an analytically pure sample; m.p. 148°-150° C. (decomp).

Anal Calcd. for $C_{20}H_{28}N_6Cl_2O_{12}$: C, 39.04; H, 4.59; N, 13.66; Cl, 11.52. Found: C, 39.09; H, 4.53; N, 13.78; Cl, 11.69.

EXAMPLE 3

Di-N,N-(N-2-chloroethyl-N-nitrosocarbamoyl)-neo-inosadiamine-1,4

(TE-17)

neo-Inosadiamine-1,4 (0.3 g.)[3] was dissolved in warm (40 ml.) water. After cooling at ambient temperature, 2-chloroethyl isocyanate (0.5 ml.) was added to the solution with agitation. The reaction mixture was settled overnight in a refrigerator and crystalline precipitates were collected by filtration. The product was washed with ethyl acetate to give di-N,N-(N-2-chloroethyl-carbamoyl)-neo-inosadiamine-1,4 (0.55 g., 84% yield); m.p. 237°-238° C.

[3] F. W. Lichtenthaler and H. O. L. Fischer, *J. Amer. Chem. Soc.*, 83, 2005-2012 (1961).

Anal Calcd. for $C_{12}H_{22}N_4Cl_2O_6$: C, 37.00; H, 5.70; N, 14.39; Cl, 18.21. Found: C, 37.04; H, 5.55; N, 14.43; Cl, 18.42.

A 100 mg. portion of the carbamoyl derivative was dissolved in 80% formic acid, and to the solution, sodium nitrite (100 mg.) was added with agitation at ambient temperature. After settling overnight at 5° C. in a refrigerator, the precipitate was collected by filtration and washed with ethanol to give 89 mg. (77%) of the title compound, m.p. 185°-186° C. (decomp).

Anal Calcd. for $C_{12}H_{20}N_6Cl_2O_8$: C, 32.23; H, 4.51; N, 18.79; Cl, 15.85. Found: C, 31.97; H, 4.43; N, 18.56; Cl, 15.72.

We claim:

1. A compound having the formula

wherein R represents

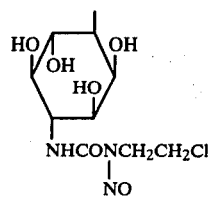 , 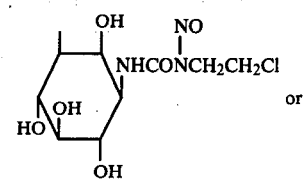 or

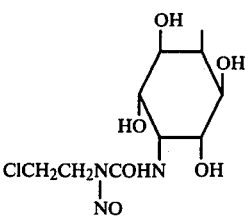 .

2. The compound of claim 1 named di-N,N-(N-2-chloroethyl-N-nitrosocarbamoyl)-myo-inosadiamine:1,4.

3. The compound of claim 1 named di-N,N-(N-2-chloroethyl-N-nitrosocarbamoyl)-myo-inosadiamine-1,3.

4. The compound of claim 1 named di-N,N-(N-2-chloroethyl-N-nitrosocarbamoyl)-neo-inosadiamine-1,4.

5. A pharmaceutical composition comprising an effective tumor-inhibiting amount of a compound of the formula

wherein R represents

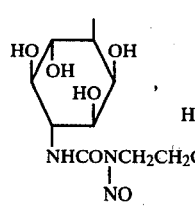 ,  or

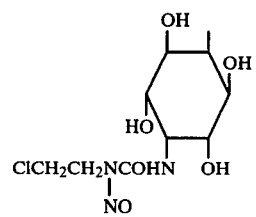 .

in combination with an inert pharmaceutically acceptable carrier or diluent.

6. A method for the inhibition in mammals of malignant tumors which comprises administering to said host an amount, effective for inhibiting said tumor, of a compound of the formula

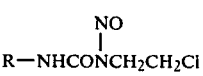

wherein R represents
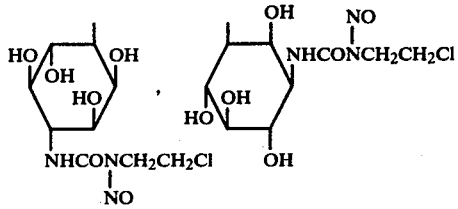 or
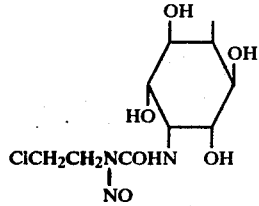
* * * * *